United States Patent [19]

Ahmed

[11] Patent Number: 5,247,154
[45] Date of Patent: Sep. 21, 1993

[54] METHOD AND APPARATUS FOR MONITORING THE LASER MARKING OF A BAR CODE LABEL

[75] Inventor: Hassan J. Ahmed, Irmo, S.C.

[73] Assignee: Westinghouse Electric Corp., Pittsburgh, Pa.

[21] Appl. No.: 642,741

[22] Filed: Jan. 17, 1991

[51] Int. Cl.5 .............................................. B23K 26/02
[52] U.S. Cl. ................................. 219/121.83; 235/462; 376/248; 382/8
[58] Field of Search ........................ 219/121.83, 121.67, 219/121.68, 121.69, 121.78, 121.82, 121.85; 364/474.08, 575, 474.24, 474.29, 474.05; 382/8, 25, 28; 235/462, 385, 465; 376/450, 452, 901, 248

[56] References Cited

U.S. PATENT DOCUMENTS

| | | | |
|---|---|---|---|
| 4,339,745 | 7/1982 | Barber et al. | 340/146.3 F |
| 4,587,407 | 5/1986 | Ahmed et al. | 235/465 |
| 4,720,618 | 1/1988 | Stamer et al. | 219/121.61 |
| 4,731,863 | 3/1988 | Sezan et al. | 382/51 |
| 4,822,987 | 4/1989 | Goldenfield et al. | 235/462 |
| 4,918,611 | 4/1990 | Shyu et al. | 364/474.08 |
| 4,922,077 | 5/1990 | Gordon | 219/121.68 |
| 4,978,917 | 12/1990 | Goldenfield et al. | 235/462 |
| 5,012,524 | 4/1991 | Le Beau | 382/8 |
| 5,091,284 | 2/1992 | Bradfield | 219/121.68 |

FOREIGN PATENT DOCUMENTS

61-131074  6/1986  Japan .................................. 235/462

Primary Examiner—Geoffrey S. Evans
Attorney, Agent, or Firm—J. C. Spadacene

[57] ABSTRACT

A method and apparatus for monitoring the laser marking of a bar code label which has been laser marked onto the end of a nuclear fuel tube for unacceptable depth penetration of the heat affected zone. The average gray level value of the bar code label positioned on the end of the nuclear fuel tube is compared with a predetermined standard. In the method disclosed, a bar code label positioned on the surface of the nuclear fuel tube is optically sensed and a set of discrete digital values representative of the depth penetration of the heat affected zone is generated. The average digital value representative of the bar code label is calculated and the average digital value compared to a predetermined standard.

11 Claims, 3 Drawing Sheets

METHOD AND APPARATUS FOR MONITORING THE LASER MARKING OF A BAR CODE LABEL

FIELD OF THE INVENTION

This invention relates to a method and apparatus for monitoring the laser marking of a bar code label for unacceptable depth penetration of the heat affected zone, and more particularly, to a method and apparatus for monitoring the laser marking of a bar code label which has been laser marked onto the end of a nuclear fuel tube for unacceptable depth penetration of the heat affected zone.

BACKGROUND OF THE INVENTION

In the manufacture of nuclear fuel tubes, the fuel tubes are marked for identification with a bar code label which is laser marked onto the end of a fuel tube. The bar code label remains an identifying indicia of a particular fuel tube throughout the manufacturing process and in the loading of the reactor core. Typically, the fuel tubes are inserted into a laser marking chamber where they are laser marked in a predominantly oxygen atmosphere. The actual bar code label mark is produced during oxidation of the surface of the fuel tube when energy from the laser is directed onto the tube surface. This oxidized surface forming the bar code label typically is superficial. However, the actual penetration of the heat affected zone, is a critical parameter of the laser marking process and requires close monitoring. The heat affected zone is that depth into the tube wall surface which is affected by the laser energy and suffers some change in metal characteristics.

Typically, about no greater than twelve percent of the tube wall penetration of the heat affected zone is desirable. Any greater percentage of heat affected zone penetration is not desirable. Of secondary importance, is too shallow a depth of penetration of the heat affected zone. For example, if the oxygen content in the laser marking chamber is too low, such as when an oxygen gas line is broken or an oxygen gas flow valve is malfunctioning, the penetration of the heat affected zone will be shallow and the actual gray level of the bar code label will be too light in appearance, i.e. a low shade of gray, and impractical for positive identification during manufacturing and fuel tube loading. Sufficient heat was not generated in this instance. On the other hand, and of greater primary concern is the possibility of too deep a heat affected zone penetration. If the laser experiences excursions, such as resulting from power line fluctuations, laser lamp aging or laser tube to laser source geometry changes, the depth of the heat affected zone will be greater than desired, and as a result, the fuel tube structural integrity could be weakened. In such instances when the heat affected zone is greater than desired, the average gray level on the bar code label will be darker than the average gray level of a bar code label having an acceptable bar code label and depth of penetration of the heat affected zone.

Heretofore, current quality control and inspection techniques utilize destructive testing of laser marked tube samples and metallographic measurement of the heat affected zone. Typically, a tube sample from a random lot is broken and the tube sample having the bar code label thereon is etched and the depth of the heat affected zone measured under the microscope to monitor the laser marking. If a tube is determined as unacceptable, the laser or the oxygen content of the laser marking chamber is adjusted as necessary. This type of destructive testing is impractical because it results in the destruction of possibly good fuel tubes, and additionally, random sampling of fuel tubes for destructive testing is not a 100% tube verification system. There may be tubes that are not part of a sampled lot which suffer undesirable depth penetration of the heat affected zone. It is more desirable to test the tube with a known parameter such as the average gray level of the bar code label which changes to a darker level as the depth of the heat affected zone increases.

Therefore, it is an object of the present invention to provide a method and apparatus of monitoring the laser marking of a bar code label on a surface such as the end of a nuclear fuel tube for unacceptable depth penetration of the heat affected zone and which is non-destructive in nature and overcomes the deficiencies of the prior art.

It is still another object of the present invention to provide a method and apparatus for monitoring the laser marking of a bar code label on a surface such as the end of a nuclear fuel tube for unacceptable depth penetration of the heat affected zone and which utilizes the average gray level of the bar code label as a comparison with a known, predetermined standard.

SUMMARY OF THE INVENTION

In the present invention, the laser marking of a bar code label on a surface, such as the end of nuclear fuel tube, is monitored for unacceptable depth penetration of the heat affected zone by comparing the average gray level value of a bar code label positioned on a surface with a predetermined standard. In the preferred method, the bar code label positioned on the surface is optically sensed. A set of discrete digital values representative of the bar code label is generated and the average digital value representative of the sensed bar code label is calculated. This average digital value is compared to a predetermined standard and the bar code is rejected when the calculated average digital value is greater or less than the predetermined standard.

The predetermined standard comprises a range of digital values having upper and lower limits defining upper and lower thresholds. The predetermined standard is established by optically sensing a plurality of acceptable bar code labels which have been laser marked on comparable surfaces as that of the surface of bar code label to be tested. A plurality of sets of discrete digital values representative of the acceptable bar code labels is generated and an average digital value calculated for the plurality of acceptable bar code labels. The predetermined standard is established from the average digital value and an upper and lower threshold limit is established based on the average digital value. The method and apparatus in accordance with the present invention preferably is used in the inspection of laser marking of bar code labels onto the ends of nuclear fuel tubes.

BRIEF DESCRIPTION OF THE DRAWINGS

Some of the objects and advantages of the present invention having been stated, others will be more fully understood by reference to the following drawings in which.

DETAILED DESCRIPTION OF THE PREFERRED EMBODIMENT

Figure 1:
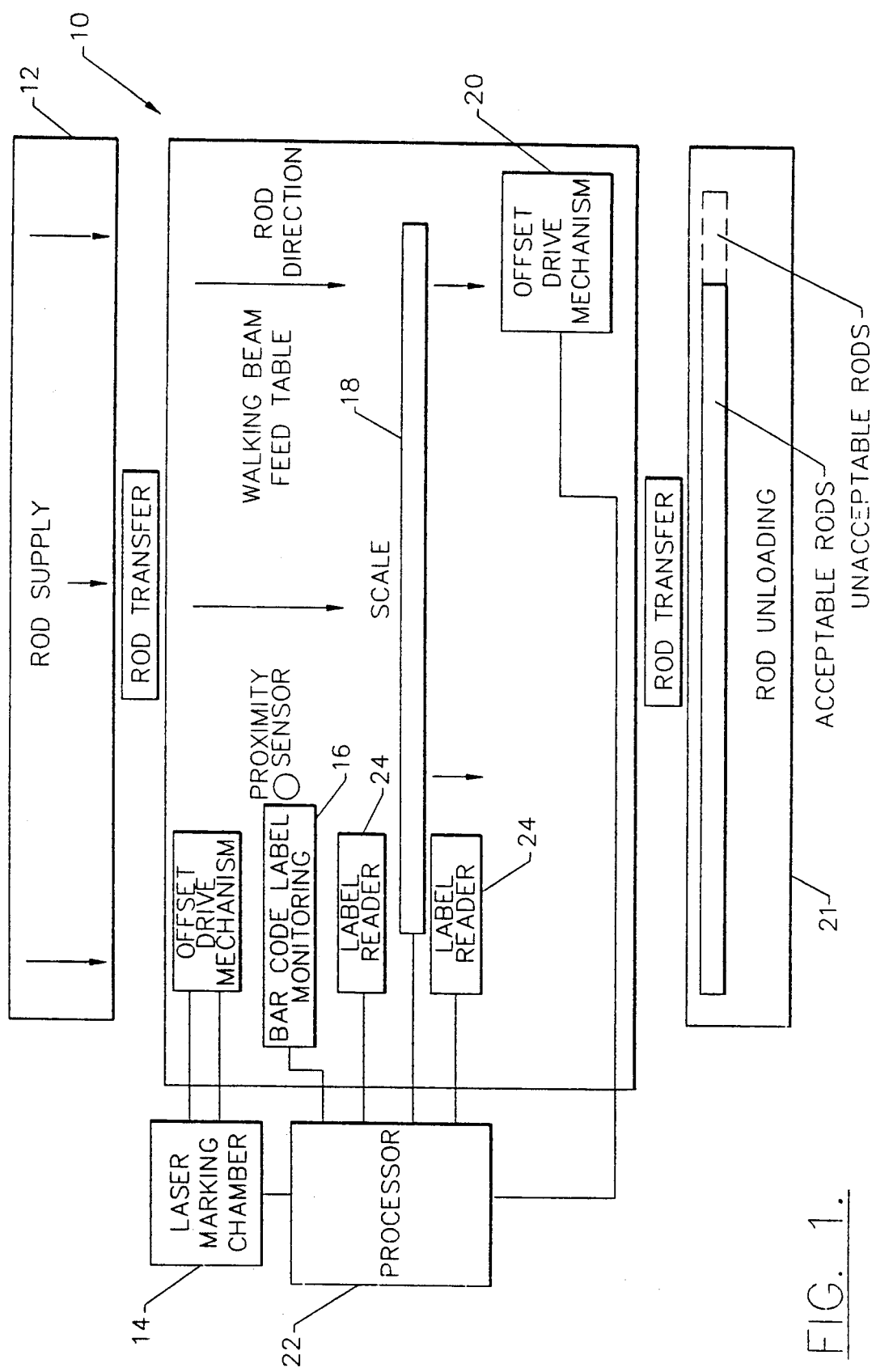
FIG. 1 is a schematic plan view of a tube marking table used in the manufacture of nuclear fuel tubes and which includes the method and apparatus for monitoring the laser marked bar code labels in accordance with the present invention.
Figure 2:
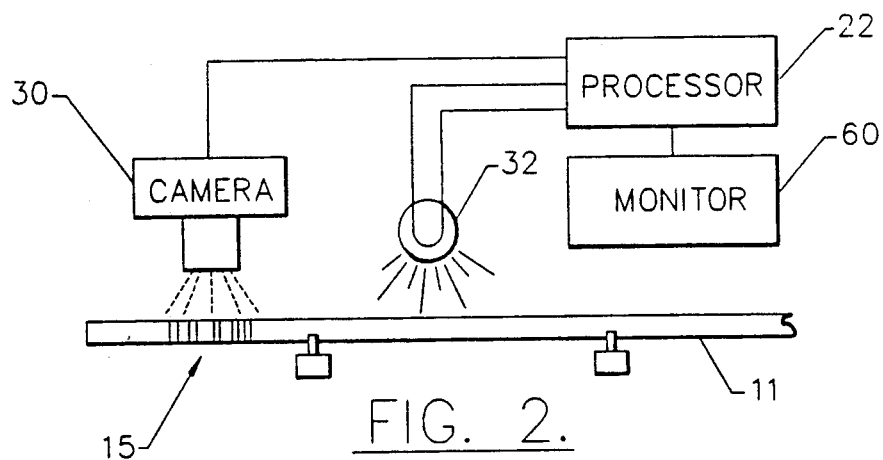
FIG. 2 is a schematic illustration of the method and apparatus for monitoring laser marking of a fuel tube.

Referring now more particularly to FIG. 1, there is disclosed schematically a tube marking table 10 in which nuclear fuel tubes 11 are transferred from a nuclear fuel tube supply table 12 and moved laterally across the table by a conventional walking beam assembly. During movement across the table each tube is offset individually into a laser marking chamber 14 where the tube ends are laser marked by a laser of approximately 50 kilowatt power with an identifying bar code label 15 (FIG. 2). After the tube end is marked in the laser marking chamber, the bar code label is monitored at a monitoring station, illustrated by the block numbered 16 where the average gray level of the bar code label is compared with a predetermined standard in accordance with the present invention. Although the invention will be described with reference to the manufacture of nuclear fuel tubes and the monitoring of the bar code labels thereon, it is understood that the method and apparatus of the present invention can be used for monitoring bar code labels which are laser marked on numerous different surfaces.

After the bar code label 15 on tube 11 is monitored, the tube is moved by the walking beam assembly and the label 15 read for identification. The tube 11 is then weighed On a scale 18. Throughout this operation, tubes 11 are transferred from the tube supply table 12 onto the tube marking table 10, and as one tube is moved into various tube positions such as laser marking, another tube 11 is transferred into another position, e.g., as where the bar code label 15 on the tube is monitored. If the bar code label is determined defective, i.e., the heat affected zone is too deep or too shallow, the fuel tube 11 is offset by a conventional offset drive mechanism 20 from other tubes and then transferred onto the tube unloading table 21. A processor 22 controls operation of the tube supply table 12 and the conventional bar code label readers 24 which are operatively connected to the processor 22 to ensure proper identification of each tube 11 during weighing and offsetting of unacceptable tubes. If any tubes are offset because they are unacceptable, an inspector visually can identify the unacceptable tubes and segregate the unacceptable tubes to a holding bin or other area.

The fuel tubes are laser marked with an identifying bar code label 15 in an oxygen-argon atmosphere which is provided in the laser marking chamber 14. The actual bar code label 15 mark is produced when the fuel tube 11 surface is oxidized after the energy output from the laser contacts the tube surface. The bar code label 15 used on the fuel tube 11 typically has 54 lines, some narrow and some wide as is conventional with most identifying bar code labels.

The illustrated nuclear fuel tubes typically are formed of zirconium and are approximately 0.375 inches in diameter and have a wall thickness of about 0.018 to about 0.020 inches. During laser marking, the desired actual depth penetration of the heat affected zone is desirably no greater than twelve percent, and an optimum value is about eight to ten percent, i.e. about 0.002 inches for the heat affected zone depth penetration. Of secondary importance, is the minimum depth penetration which desirably is only about six or seven percent. Too shallow a depth of penetration of the heat affected zone will not affect the tube metal, but the bar code label will have a light appearance, i.e. low shade of gray. A lesser depth penetration of the heat affected zone is not desirable because the bar code label marking will be very light, i.e., a low shade of gray, and thus not practicable for identification purposes. Additionally, a light shade of gray and poor depth penetration could result in a fuel tube bar code label which will wear quickly from the end of the fuel tube.

Figure 3A:
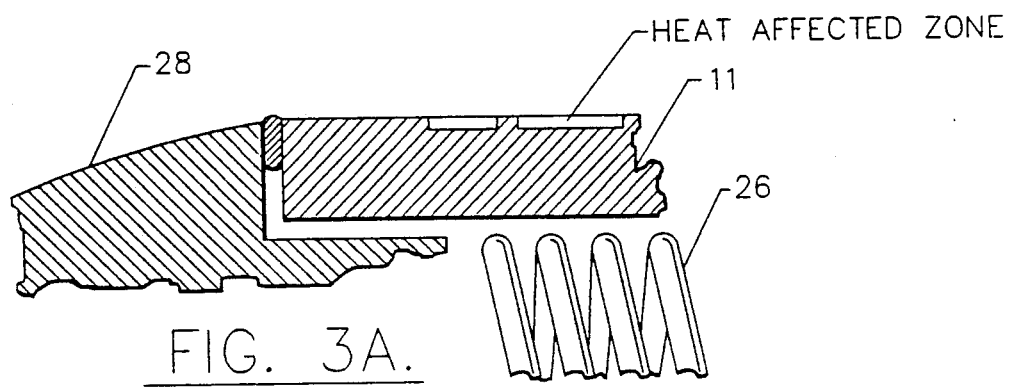
FIGS. 3A through 3C are schematic, sectional views of the end of fuel tubes after having sealing plugs and fuel pellets added thereto and showing various depth penetrations of the heat affected zone.

More importantly if the depth of the heat affected zone is greater than desired, such as when the laser beam experiences excursions from line power fluctuations, laser lamp aging, and tube to laser source geometry changes, the fuel tube could be weakened at the point of laser penetration. In such a case, the bar code label marking will be very dark as compared to a more desirable bar code label marking of normal and desired heat affected zone depth penetration. Identification of the bar code label in this case will not be a problem. However, the fuel tube could be weakened at the point of laser penetration and undesirable results can occur. For example, often, the fuel tubes contain a spring 26 which is positioned against the sealing plug 28 (FIG. 3A). The sealing plug is welded to the fuel tube 11 and the spring 26 positioned against the sealing plug 28 biases the nuclear fuel pellets (not shown) held in the fuel tube against each other. If the depth of the heat affected zone is greater than desired, the generated heat could adversely affect the resiliency of the spring, the biasing of the pellets, and thus affect fissionable operation of the nuclear fuel tube.

As noted before, the bar code label gray level is a function of the laser power and oxygen content in the laser marking chamber 14. The heat affected zone at the marking area is a linear function of the laser beam energy. Therefore, the gray level of the bar code label marking is a good indicator of both the oxygen flow and the laser energy and one or the other can be adjusted after a tube 11 is monitored and determined as having a defective depth penetration of the heat affected zone. The present invention compares the average gray level of a bar code label with a predetermined standard for determining whether the depth penetration of the heat affected zone is acceptable.

Referring now to FIG. 2, the bar code label monitoring system includes a video camera 30 which can be of the conventional type of commercially available video camera such as a Fairchild CCD camera (with appropriate lens) for obtaining a two-dimensional image of a target area on the tube containing the bar code label 15 which has been laser marked thereon. The bar code label 15 is illuminated by a light source 32 which may be an ordinary room fluorescent light. It will also be understood by those having skill in the art that the illumination frequency also can be varied to obtain the desired results. The video camera 30 can be a high resolution video color camera which is operated in black-andwhite mode to obtain a high resolution video signal. The video camera 30 is coupled to a general all purpose data processor 22 which includes hardware and software for digitizing the video signal to obtain 512×512×8 bits of gray scale intensity data and for obtaining the average gray scale value. It will also be understood by those having skill in the art that digitized gray scale data can be produced by a video camera so that the processor need only compute the average gray scale value.

Figure 4:
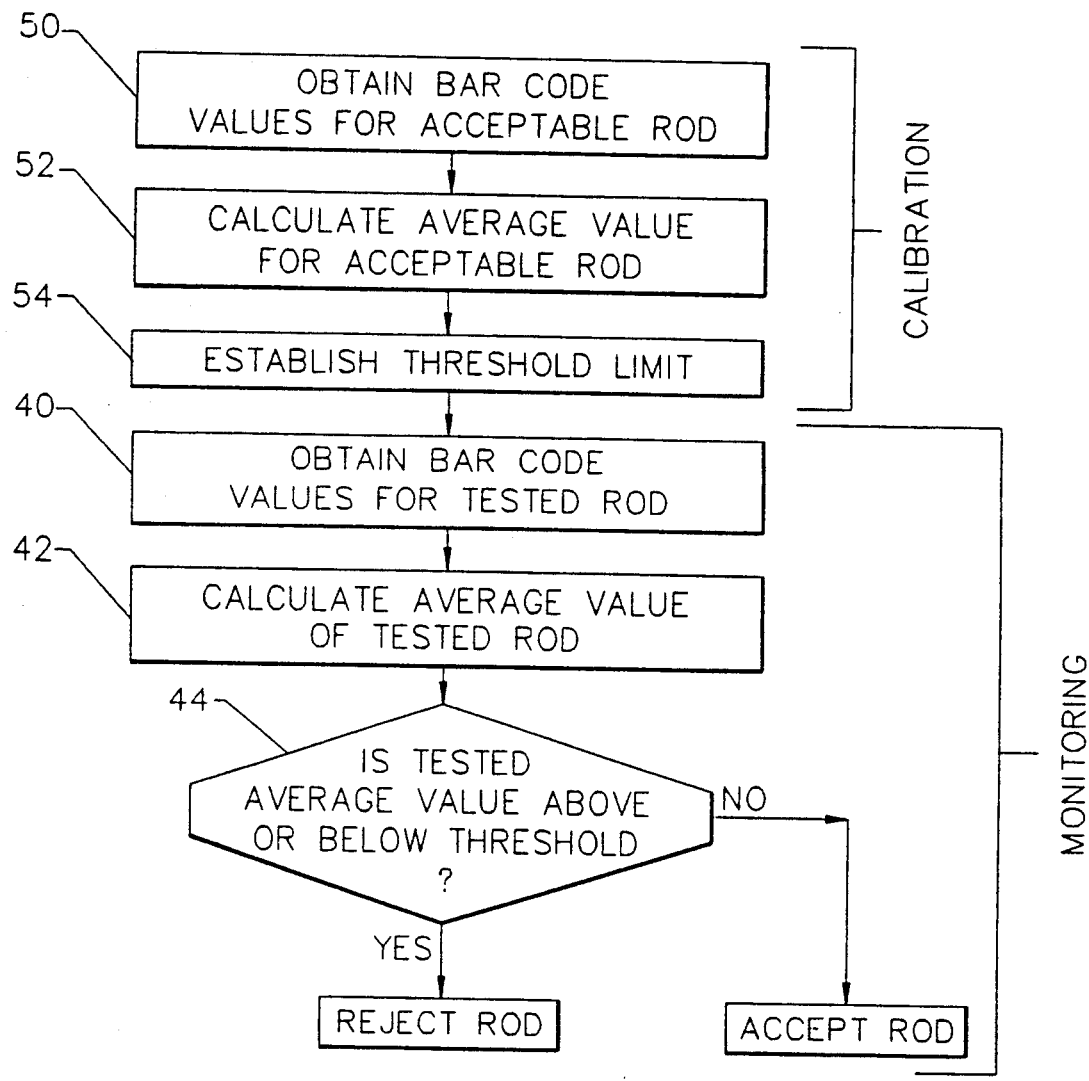
FIG. 4 is a flow chart schematically illustrating the operations performed by the processor of FIGS. 1 and 2 for monitoring the depth penetration of the heat affected zone.

Referring now to FIG. 4, the operations performed by the processor of FIGS. 1 and 2 will now be described. During monitoring of a fuel tube for unacceptable depth penetration of a bar code label which has been laser marked thereon, the processor obtains the gray scale values for the bar code label sensed area, either directly or by digitizing the camera video signal as shown at block 40. The control of the camera by a processor is well known to those having skill in the art and need not be described in further detail. Once a 512×512 digital image array is obtained, all the gray scale values for the points are summed and that summed value is divided by the number of values, i.e., 512×512, at block 42 to calculate an average digital value for the bar code label of the tested fuel tube. This average value is compared with a predetermined standard defined by an upper and lower threshold value. If the average value is above or below that threshold value, the tube is rejected as shown in block 44. When a tube is determined defective, it is offset from other tubes by conventional tube offset drive means 46 on the tube marking table 10 as shown in FIG. 1.

It will be understood by those having skill in the art that the predetermined standard value (for an acceptable bar code label) is preset in the processor 22 based upon previously measured or calculated values. Typically, a plurality of known, acceptable bar code labels on a plurality of tubes are optically sensed to obtain a plurality of sets of discrete digital values representative of the acceptable bar code labels for each known fuel tube at block 50. The average digital value for the plurality of acceptable bar code labels is calculated at block 52 and the predetermined standard established from the average digital value at block 54. The predetermined standard preferably is a range of values having upper and lower threshold limits which define an acceptable range of gray scale values corresponding to a percentage range of depth penetration, i.e., seven to twelve percent. For example, if sixty-four levels of gray are analyzed and discerned by the processor, and the preferred average gray level for an acceptable plurality of tubes is forty, then a range of values between thirty-five and forty-five of gray level would be acceptable. During scanning of the end of the nuclear fuel tube, other areas adjacent the bar code label also will be scanned. The software includes an appropriate algorithm to filter out ambient light effects. The portion of the tube without the bar code label thereon forms the background. The pixels of the background are contrasted with the pixels of the bar code label to filter out ambient light. The amount of light may vary depending on factors such as the bulb or other ambient light. Thus, the actual reflectivity of the tube varies. In the calibration of the system, it is understood that a single nuclear fuel tube having an acceptable bar code label thereon also could be used. However, it is more desirable to use a plurality of fuel tubes each having an acceptable bar code label thereon for establishing the predetermined standard. Throughout the monitoring, a histogram chart can be displayed on a visual monitor evidencing the results of the monitoring activities (block 60).

Figure 3B:
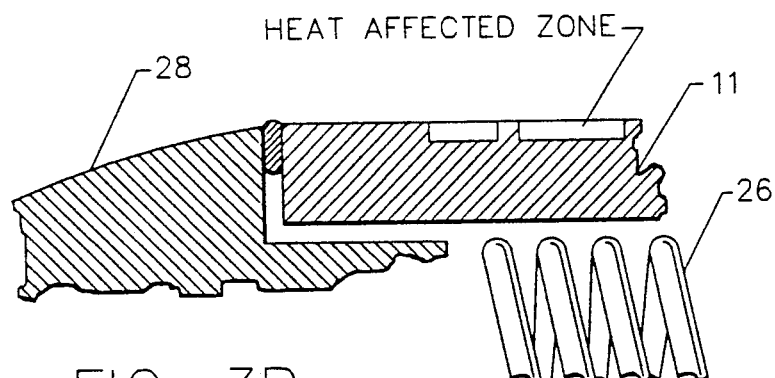
Figure 3C:
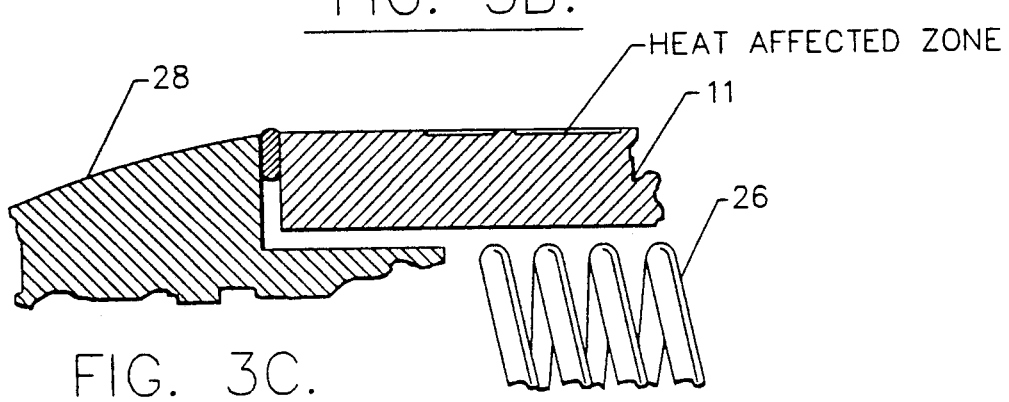

As illustrated now in FIGS. 3A through 3C, there is shown in schematic a portion of three depth penetrations of the heat affected zone on the end of a nuclear fuel tube 11. FIG. 3A shows an acceptable depth penetration of the heat affected zone Which is in the range of about ten percent of the tube wall thickness. This depth penetration of the heat affected zone will have an average gray scale within the predetermined standard. FIG. 3B illustrates an unacceptable depth penetration of the heat affected zone. Although the darkness of the bar code label is acceptable for readability, the heat affected zone is much too deep and may adversely affect the tube and any spring positioned in the tube and adjacent the sealing plug. This tube will be rejected. FIG. 3C illustrates shallow penetration of the heat affected zone and is very light, i.e. a low shade of gray. The average gray scale value of that mark will be above the predetermined standard and this tube will be rejected.

In the drawings and specification there have been disclosed the typical preferred embodiment of the invention and, although specific terms are employed, they are used in a generic and descriptive sense only and not for purposes of limitation, the scope of the invention being set forth in the following claims.

I claim:

1. A method of monitoring the laser marking of a bar code label on a surface of an object for unacceptable depth penetration of the heat affected zone associated with the bar code label, comprising the steps of optically sensing a bar code label which has been laser marked on the surface of an object to determine the depth penetration of the heat affected zone associated with the bar code label, generating a set of discrete digital values representative of the depth penetration of the heat affected zone, calculating an average digital value representative of the depth penetration of the heat affected zone, comparing the average digital value to a predetermined range of digital values, and rejecting a bar code label when the calculated average digital value is outside the predetermined range.

2. The method according to claim 1 including the step of establishing the predetermined range of digital values by optically sensing the depth penetration of the heat affected zone of an acceptable bar code label which has been laser marked on a surface of an object, generating a set of discrete digital values representative of the depth penetration of the heat affected zone of the acceptable bar code label, calculating an average value for the set of discrete digital values, and establishing a predetermined range from the calculated average value.

3. The method according to claim 2 wherein the step of establishing the predetermined range of digital values includes calculating an average value from a plurality of sets of digital values representative of the depth of penetration of the heat affected zone of each of a plurality of optically sensed acceptable bar code labels.

4. A method of monitoring the laser marking of a bar code label on a tube for unacceptable depth penetration of the heat affected zone associated with the bar code label, comprising the steps of generating a two dimensional image having a two dimensional array of digital values representative of the depth penetration of the heat affected zone associated with a bar code label which has been laser marked on a predetermined area of the surface of a tube, calculating an average digital value corresponding to the depth penetration of the heat affected zone, comparing the average digital value to a predetermined range of digital values having upper and lower limits defining upper and lower thresholds, and rejecting a tube when the calculated average digital value is greater than the upper limit or less than the lower limit of the predetermined range.

5. The method according to claim 4 including the step of monitoring a plurality of tubes in sequence and offsetting from acceptable tubes these tubes which have been monitored as having unacceptable bar code labels.

6. A method of monitoring the laser marking of a bar code label on a tube for unacceptable depth penetration of the heat affected zone associated with the bar code label, comprising the steps of generating a two dimensional digital image having a two dimensional array of digital values representative of the depth penetration of the heat affected zone of an acceptable bar code label which has been laser marked onto the surface of a tube, calculating an average value for the array of digital values representative of the depth penetration of the heat affected zone of the acceptable bar code label, determining a predetermined range of digital values having upper and lower limits defining upper and lower thresholds from the average value, generating a two dimensional digital image having a two dimensional array of digital values representative of the depth penetration of the heat affected zone of a bar code label positioned on the surface of an unknown tube, calculating an average value for the array of digital values representative of the depth penetration of the heat affected zone of the unknown bar code label, comparing the calculated average value with the predetermined range of digital values, and rejecting a tube when the calculated average digital value is greater than the upper limit or less than the lower limit of the predetermined range.

7. A method of monitoring the laser marking of a bar code label on the end of a nuclear fuel tube for unacceptable depth penetration of the heat affected zone associated with the bar code label, comprising the steps of optically sensing a bar code label which has been laser marked onto the end of a nuclear fuel tube to determine the depth penetration of the heat affected zone associated with the bar code label, generating a set of discrete digital values representative of the depth penetration of the heat affected zone, calculating an average digital value representative of the depth penetration of the heat affected zone, comparing the average digital value to a predetermined range of digital values, and rejecting a fuel tube when the calculated average value is greater or less than the predetermined range.

8. A method of monitoring the laser marking of a bar code label on a nuclear fuel tube for unacceptable depth penetration of the heat affected zone associated with the bar code label comprising the steps of comparing the average gray level value of a bar code label which has been laser marked onto the end of a nuclear fuel tube and representative of the depth penetration of the heat affected zone with a predetermined range of gray level values having upper and lower threshold limits, and rejecting the fuel tube if the average gray level value is greater than the upper limit or less than the lower limit of the predetermined range.

9. An apparatus for monitoring the laser marking of a bar code label on the surface of a nuclear fuel tube for unacceptable depth penetration of the heat affected zone associated with the bar code label, comprising means for optically sensing a bar code label which has been laser marked onto the surface of a fuel tube to determine the depth penetration of the heat affected zone associated with the bar code label, means for generating a set of discrete digital values representative of the depth penetration of the heat affected zone, means for calculating an average digital value representative of the depth penetration of the heat affected zone, means for comparing the average digital value to a predetermined range of digital values having upper and lower threshold limits, and means for rejecting a tube when the calculated average digital value is greater than the upper limit or less than the lower limit of the predetermined range.

10. The apparatus according to claim 9 wherein the optically sensing means is a video imaging device.

11. The apparatus according to claim 9 wherein the rejecting means comprises means for translating tubes across a platform, and means for offsetting a tube when the calculated average digital value of such tube is greater than the upper limit or less than the lower limit of the predetermined range.

* * * * *